US011465950B2

(12) United States Patent
Jin et al.

(10) Patent No.: US 11,465,950 B2
(45) Date of Patent: Oct. 11, 2022

(54) AROMATIZATION OF LIGHT HYDROCARBONS USING METAL-DOPED ZEOLITE CATALYSTS WITH ENHANCED MESOPOROSITY

(71) Applicants: Saudi Arabian Oil Company, Dhahran (SA); King Fahd University of Petroleum and Minerals, Dhahran (SA)

(72) Inventors: Yaming Jin, Dhahran (SA); Ziyauddin S. Qureshi, Dhahran (SA); Abdullah M. Aitani, Khobar (SA); Omer Refa Koseoglu, Dhahran (SA); Mohammad Naseem Akhtar, Dhahran (SA); Hassan Saeed Al-Awad Alasiri, Dhahran (SA)

(73) Assignees: Saudi Arabian Oil Company, Dhahran (SA); King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 17/011,008

(22) Filed: Sep. 3, 2020

(65) Prior Publication Data
US 2022/0064082 A1   Mar. 3, 2022

(51) Int. Cl.
| | |
|---|---|
| *C07C 2/42* | (2006.01) |
| *B01J 23/06* | (2006.01) |
| *B01J 23/08* | (2006.01) |
| *B01J 29/40* | (2006.01) |
| *B01J 35/10* | (2006.01) |
| *B01J 37/00* | (2006.01) |
| *B01J 37/04* | (2006.01) |
| *B01J 37/08* | (2006.01) |
| *C10G 35/06* | (2006.01) |
| *C10G 35/095* | (2006.01) |

(52) U.S. Cl.
CPC .............. *C07C 2/42* (2013.01); *B01J 23/06* (2013.01); *B01J 23/08* (2013.01); *B01J 29/405* (2013.01); *B01J 35/1042* (2013.01); *B01J 35/1047* (2013.01); *B01J 37/0018* (2013.01); *B01J 37/04* (2013.01); *B01J 37/088* (2013.01); *C10G 35/06* (2013.01); *C10G 35/095* (2013.01); *C07C 2523/06* (2013.01); *C07C 2523/08* (2013.01); *C07C 2529/04* (2013.01); *C07C 2529/40* (2013.01); *C10G 2300/1037* (2013.01); *C10G 2300/70* (2013.01)

(58) Field of Classification Search
CPC ... C07C 2/42; C07C 2523/06; C07C 2523/08; C07C 2529/04; C07C 2529/40; C10G 35/06; C10G 35/095; C10G 2300/70; C10G 2300/1037

USPC ........ 208/134, 135, 141; 585/407, 415, 422, 585/446, 467, 468, 417
See application file for complete search history.

(56) References Cited

U.S. PATENT DOCUMENTS

| | | | |
|---|---|---|---|
| 3,756,942 A | 9/1973 | Cattanach | |
| 3,953,366 A | 4/1976 | Morrison | |
| 4,157,293 A | 6/1979 | Plank et al. | |
| 4,330,396 A | 5/1982 | Miller | |
| 4,861,934 A | 8/1989 | Suzuki et al. | |
| 5,055,437 A | 10/1991 | Herbst et al. | |
| 5,073,673 A | 12/1991 | Hirabayashi et al. | |
| 5,276,232 A | 1/1994 | Inoue et al. | |
| 5,958,216 A | 9/1999 | Glover | |
| 6,177,002 B1 | 1/2001 | Glover | |
| 7,285,696 B2 * | 10/2007 | Schmidt .................. | B01J 29/40 |
| | | | 585/467 |
| 10,427,142 B1 * | 10/2019 | Al-Herz .................. | C01B 39/36 |
| 10,519,387 B2 | 12/2019 | Ravishankar et al. | |
| 10,596,558 B2 | 3/2020 | Arvind et al. | |
| 11,021,422 B1 | 6/2021 | Koseoglu | |
| 2004/0110630 A1 | 6/2004 | Schmidt et al. | |
| 2004/0236164 A1 | 11/2004 | Rangarajan et al. | |
| 2011/0132804 A1 | 6/2011 | Stevenson et al. | |
| 2012/0277503 A1 | 11/2012 | Wegerer et al. | |
| 2012/0283494 A1 | 11/2012 | Smith et al. | |
| 2014/0316179 A1 | 10/2014 | Ghosh et al. | |
| 2016/0030931 A1 * | 2/2016 | Kelkar .................... | B01J 37/30 |
| | | | 585/240 |
| 2017/0088485 A1 | 3/2017 | Shekyar et al. | |
| 2017/0114288 A1 | 4/2017 | Ravishankar et al. | |
| 2017/0144138 A1 | 5/2017 | Arvind et al. | |
| 2017/0305812 A1 | 10/2017 | Keusenkothen et al. | |
| 2018/0066197 A1 | 3/2018 | Koseoglu et al. | |
| 2018/0305273 A1 | 10/2018 | Patel et al. | |
| 2019/0224653 A1 | 7/2019 | Koseoglu et al. | |
| 2020/0407649 A1 | 12/2020 | Lapinski et al. | |
| 2022/0025276 A1 | 1/2022 | Koseoglu et al. | |

FOREIGN PATENT DOCUMENTS

CN            106552663 A       4/2017

OTHER PUBLICATIONS

Kanai et al., "Aromatization of N-Hexane over ZnOH— ZSM-5 catalysts", Journal of Catalysis, vol. 114, Issue 2, Dec. 1988, abstract only.*
Office Action dated May 28, 2021 pertaining to U.S. Appl. No. 17/010,969, filed Sep. 3, 2020, 16 pages.
Aitani et al., "Catalytic Upgrading of Light Naphtha to Gasoline Blending Components: A Mini Review", Energy & Fuels, vol. 33, pp. 3828-3843, 2019.

(Continued)

*Primary Examiner* — Elizabeth D Wood
(74) *Attorney, Agent, or Firm* — Dinsmore & Shohl LLP

(57) ABSTRACT

According to embodiments, a process for aromatizing hydrocarbons may include contacting the hydrocarbons with a zinc- or gallium-doped ZSM-5 catalyst having a mesopore volume of greater than 0.09 cm$^3$/g. Contacting the hydrocarbons with the catalyst causes a least a portion of the hydrocarbons to undergo chemical reactions to form aromatic hydrocarbons.

14 Claims, 1 Drawing Sheet

(56) References Cited

OTHER PUBLICATIONS

Bhan et al., "Propane Aromatization over HZSM-5 and Ga/HZSM-5 Catalysts", Catalysis Reviews, vol. 50, pp. 19-151, 2008.

Dicksson et al., "The Future of Petrochemicals: Growth Surrounded by Uncertainty", Deloitte, New York, 2019.

Hodala et al., "Aromatization of C5-rich Light Naphtha Feedstock over Tailored Zeolite Catalysts: Comparison and Model Compounds (n-C5-n-C7)", ChemPubSoc Europe, Chemistry Select, 1, pp. 2515-2521, 2016.

Meriaudeau et al., "Dehydrocyclization of Alkanes Over Zeolite-Supported Metal Catalysts: Monofunctional or Bifunctional Route", Catalysts Reviews, vol. 39, pp. 5-48, 1977.

Ono, "Transformation of Lower Alkanes into Aromatic Hydrocarbons over ZSM-5 Zeolites", Catalysts Reviews, Science and Engineering, vol. 34, pp. 179-226, 1992.

Su et al., "Synergic Effect of GaO+/Bronsted Acid in Hierarchical Ga/Al— ZSM-5 Bifunctional Catalysts for 1-Hexene Aromatization", Industrial & Engineering Chemistry Research, vol. 58, pp. 20543-20552, 2019.

Tamiyakul et al., "Generation of reductive Zn species over Zn/HZSM-5 catalysts for n-pentane aromatization", Applied Catalystis A: General, vol. 525, pp. 190-196, 2016.

Tshabalala et al., "Aromatizatin of n-hexane over Ga, Mo and Zn modified H-ZSM-5 zeolite catalyst", Catalysis Communications, vol. 72, pp. 49-52, 2015.

Verboekend et al., "Full Compositional Flexibility in the Preparatijn of Mesoporous MFI Zeolites by Desilication", The Journal of Physical Chemistry, 48 pgs., 2011.

Wannapakdee et al., "Aromatization of C5 hydrocarbons over Ga-modified hierarchical HZSM-5 nanosheets", Fuel, vol. 236, pp. 1243-1253, 2019.

Youming et al., "Aromatization of Methanol over La/Zn/HZSM-5 Catalysts", Catalysis, Kinetics and Reactors, Chinese Journal of Chemical Engineering, vol. 19, No. 3, pp. 439-445, 2011.

U.S. Office Action dated Dec. 30, 2021 pertaining to U.S. Appl. No. 17/010,969, filed Sep. 3, 2020, 17 pages.

International Search Report and Written Opinion dated Nov. 26, 2021 pertaining to International application No. PCT/US2021/048630 filed Sep. 1, 2021, 15 pages.

Agaeva, S. B. et al. "Product Control in Catalytic Aromatization of C2+ Hydrocarbons", Petroleum Chemistry, vol. 47, No. 3, May 1, 2007, pp. 162-166.

Tuktin, Balga Tuktievich et al. "Catalytic Conversion of Light Hydrocarbons into Aromatic Hydrocarbons over Modified Zeolite Catalysts", Oriental Journal of Chemistry, vol. 33, No. 4, Aug. 28, 2017, pp. 1799-1804.

Ellouh, Mohammed et al. "Light Paraffinic Naphtha to BTX Aromatics over Metal-Modified Pt/ZSM-5", Chemistryselect, vol. 5, No. 44, Nov. 30, 2020, pp. 13807-13813.

International Search Report and Written Opinion dated Dec. 2, 2021 pertaining to International application No. PCT/US2021/048789 filed Sep. 2, 2021, 13 pages.

Ogunronbi, K.E. et al. "New insights into hierarchical metal-containing zeolites; synthesis and kinetic modelling of mesoporous gallium-containing ZSM-5 for propane aromatization" Journal of Molecular Catalysis A: Chemical, vol. 406, Sep. 1, 2015, pp. 1-18.

U.S. Office Action dated Mar. 31, 2022 pertaining to U.S. Appl. No. 17/338,863, filed Jun. 4, 2021, 18 pages.

\* cited by examiner

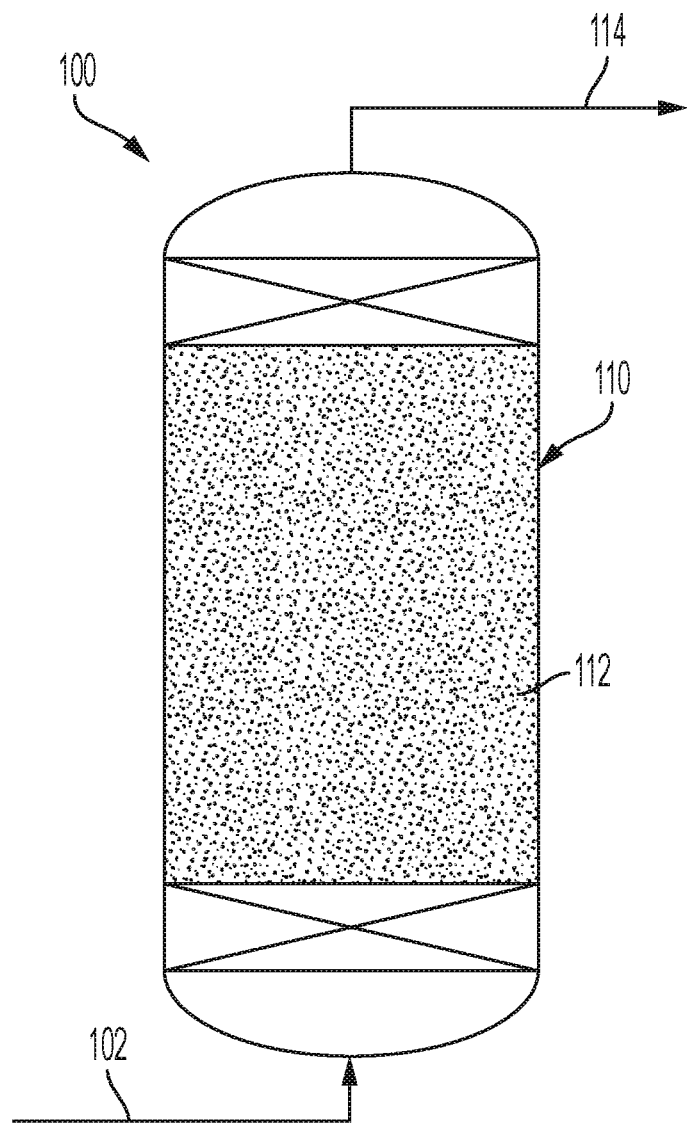

AROMATIZATION OF LIGHT HYDROCARBONS USING METAL-DOPED ZEOLITE CATALYSTS WITH ENHANCED MESOPOROSITY

TECHNICAL FIELD

The present disclosure generally relates to processing hydrocarbons and, more particularly, to aromatizing hydrocarbons using a metal-doped ZSM-5 catalyst with enhanced mesoporosity.

BACKGROUND

Light hydrocarbon feedstocks, such as naphtha, may be converted to greater value chemical products, such as aromatic compounds, through various chemical reactions. Typical hydrocarbon feedstocks contain a broad range of paraffinic, olefinic, naphthenic, and aromatic hydrocarbons that must undergo one or more chemical conversions before the greater value products are obtained. One such reaction is aromatization in which non-aromatic hydrocarbons are converted to aromatic hydrocarbons, such as benzene, toluene, ethylbenzene, and xylenes, which may be collectively referred to as "BTEX." These aromatic hydrocarbon compounds may be valuable intermediates for producing plastics, fibers, or other synthetic products.

BRIEF SUMMARY

Supported catalyst compositions, such as metal oxides supported on zeolite supports, play an integral role in hydrocarbon conversion processes. The performance of supported catalyst compositions incorporated in such processes depends at least in part on the pore structure and acid site distribution of the supported catalyst composition. However, coking, which is associated with direct aromatization of light hydrocarbons, can lead to deposition of heavy carbonaceous species, which can block active sites inside the zeolite structure and hinder products from leaving the catalyst.

Accordingly, there is a need for catalyst compositions and processes for aromatizing hydrocarbons with improved catalyst compositions to produce various greater value chemical products, such as aromatic hydrocarbon compounds. The catalyst compounds and processes of the present disclosure may include catalyst compositions having an enhanced mesoporosity, which can improve accessibility of the reactant molecules to catalyst active sites. The catalyst compositions of the present disclosure, for example, include a zinc- or gallium-doped ZSM-5 catalyst having a mesopore volume of greater than 0.09 $cm^3/g$. The enhanced mesoporosity of the catalyst compositions of the present disclosure may provide improved yield of aromatic hydrocarbon compounds from conversion of hydrocarbons through aromatization compared to existing supported catalyst compositions.

According to one or more embodiments of the present disclosure, a process for aromatizing hydrocarbons comprises contacting the hydrocarbons with a catalyst comprising a zinc- or gallium-doped ZSM-5 catalyst having a mesopore volume of greater than 0.09 $cm^3/g$. Contacting the hydrocarbons with the catalyst causes at least a portion of the hydrocarbons to undergo chemical reactions to form aromatic hydrocarbons.

According to one or more embodiments of the present disclosure, a process of forming a catalyst for aromatizing hydrocarbons comprises enhancing a mesoporosity of a zeolite support by a base-leaching treatment, an acid-leaching treatment, or both to form a zeolite support having an enhanced mesoporosity. The process further includes mixing the zeolite support having enhanced mesoporosity with a solution containing zinc or gallium to disperse the zinc or gallium on the zeolite support having enhanced mesoporosity, and calcining the zeolite support having enhanced mesoporosity with zinc or gallium dispersed thereon to form a zinc- or gallium-doped zeolite catalyst having a mesopore volume of greater than 0.09 $cm^3/g$.

Additional features and advantages of the technology disclosed in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 1A schematically depicts an upflow fixed bed continuous flow reactor, according to one or more embodiments of the present disclosure; and FIG. 1B schematically depicts a downflow fixed bed continuous flow reactor, according to one or more embodiments of the present disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to processes for aromatizing hydrocarbons including contacting the hydrocarbons with a catalyst including a zinc- or gallium-doped ZSM-5 catalyst having a mesopore volume of greater than 0.09 $cm^3/g$. Contacting the hydrocarbons with the catalyst causes a least a portion of the hydrocarbons to undergo chemical reactions to form aromatic hydrocarbons. As such, the processes for converting hydrocarbons to aromatic hydrocarbon compounds using the catalyst composition of the present disclosure may produce greater yields of aromatic compounds compared to conversion processes using existing supported catalyst compositions.

It should be understood that the hydrocarbon feed may be named for its components, and the component for which the feed is named may be the major component of the hydrocarbon feed (such as comprising from 50 weight percent (wt. %), from 70 wt. %, from 90 wt. %, from 95 wt. %, from 99 wt. %, from 99.5 wt. %, or even from 99.9 wt. % of the contents of the hydrocarbon feed to 100 wt. % of the contents of the feed).

As used throughout the present disclosure, the term "catalyst" may refer to any substance that increases the rate of a particular chemical reaction. Catalyst compositions described in the present disclosure may be utilized to promote various reactions, such as the aromatization of non-aromatic hydrocarbons.

As used throughout this disclosure, "zeolites" may refer to micropore-containing inorganic materials with regular intra-crystalline cavities and channels of molecular dimension. In embodiments, the zeolites described herein may be referred to as "mesoporous zeolites." As such, "zeolites" and "mesoporous zeolites" may be used interchangeably throughout this disclosure for embodiments which include mesopores, as is described in detail herein. Zeolites generally comprise a crystalline structure, as opposed to an amorphous structure such as what may be observed in some porous materials such as amorphous silica. Zeolites generally include a microporous framework which may be identified by a framework type. The microporous structure of zeolites (e.g., 0.3 nm to more than 1 nm pore size) may render large surface areas and desirable size-/shape-selectivity, which may be advantageous for catalysis. The zeolites described are crystalline aluminosilicates that may additionally include metals other than silicon and aluminum. In embodiments, the zeolites described may include micropores (present in the microstructure of a zeolite), and additionally include mesopores. As used throughout this disclosure, micropores refer to pores in a structure that have a diameter of less than or equal to 2 nm and greater than or equal to 0.1 nm, and mesopores refer to pores in a structure that have a diameter of greater than 2 nm and less than or equal to 50 nm. Unless otherwise described herein, the "pore size" of a material refers to the average pore size, but materials may additionally include mesopores having a particular size that is not identical to the average pore size.

Referring now to the process for aromatizing hydrocarbons, the process may include contacting hydrocarbons from a hydrocarbon feed with the catalyst composition of the present disclosure, which includes a metal oxide dispersed on the surfaces of a zeolite support. The hydrocarbon feed may include but is not limited to alkanes, alkenes, alkynes, cycloalkanes, alkadienes, or combinations of these hydrocarbons. In embodiments, the hydrocarbons may include paraffins, olefins, naphthenes, alkylbenzenes, or combinations of these hydrocarbons. The hydrocarbons in the hydrocarbon feed may have from 1 carbon atom to 30 carbon atoms, such as from 1 carbon atom to 20 carbon atoms, from 1 carbon atom to 15 carbon atoms, from 1 carbon atom to 10 carbon atoms, from 2 carbon atoms to 30 carbons atoms, from 2 carbon atoms to 20 carbon atoms, from 2 carbon atoms to 15 carbon atoms, from 2 carbon atoms to 12 carbon atoms, from 1 to 10 carbon atoms, from 4 carbon atoms to 20 carbon atoms, from 4 carbon atoms to 10 carbon atoms, or from 4 carbon atoms to 7 carbon atoms. For example, and not by way of limitation, the hydrocarbon feed to be contacted with the catalyst composition may include one or more of methane, ethane, ethene, ethyne, propane, propene, propyne, butane, butene, butyne, pentane, pentene, pentyne, hexane, hexene, hexyne, cyclohexane, cyclohexene, heptane, heptene, heptyne, octane, octene, octyne, nonane, nonene, nonyne, and combinations of these hydrocarbons.

The hydrocarbon feed may include one or more intermediate streams from a hydrocarbon processing facility, such as but not limited to light naphtha, heavy naphtha, or combinations of these. In embodiments, the hydrocarbon feed may include straight run light naphtha. In one or more embodiments, the hydrocarbon feed may include light naphtha comprising at least 50 wt. % alkanes and having a boiling point temperature of from 30 degrees Celsius (° C.) to 90° C., based on the total weight of the hydrocarbon feed. In one or more embodiments, the hydrocarbon feed may include from 50 wt. % to 99.9 wt. % alkanes, from 55 wt. % to 99.9 wt. % alkanes, from 60 wt. % to 99.9 wt. % alkanes, from 65 wt. % to 99.9 wt. % alkanes, from 70 wt. % to 99.9 wt. % alkanes, or from 75 wt. % to 99.9 wt. % alkanes, based on the total weight of the hydrocarbon feed. In one or more embodiments, the hydrocarbon feed may include from 50 wt. % to 99.9 wt. % $C_5$ and $C_6$ hydrocarbons, such as from 55 wt. % to 99.9 wt. % $C_5$ and $C_6$ hydrocarbons, from 60 wt. % to 99.9 wt. % $C_5$ and $C_6$ hydrocarbons, from 65 wt. % to 99.9 wt. % $C_5$ and $C_6$ hydrocarbons, from 70 wt. % to 99.9 wt. % $C_5$ and $C_6$ hydrocarbons, or from 75 wt. % to 99.9 wt. % $C_5$ and $C_6$ hydrocarbons, based on the total weight of the hydrocarbon feed. In embodiments, the hydrocarbon feed may include aromatic, naphthenic, or aromatic and naphthenic hydrocarbons in minor amounts by volume.

The catalyst composition may include a metal oxide dispersed on the surfaces of the zeolite support. The catalyst composition may include one or more oxides of a metal selected from groups 4 to 13 of the International Union of Pure and Applied Chemistry (IUPAC) periodic table, such as groups 8 to 13 of the IUPAC periodic table. In one or more embodiments, the metal of the one or more metal oxides may be a metal selected from groups 4 to 13 and periods 4 to 6 of the IUPAC periodic table, such as period 4 of the periodic table. The metal of the metal oxide may include, but is not limited to, titanium, vanadium, chromium, manganese, iron, cobalt, nickel, copper, zinc, gallium, molybdenum, palladium, silver, hafnium, tungsten, platinum, gold, or combinations of these metals. In one or more embodiments, the metal of the one or more metal oxides may include gallium, zinc, iron, hafnium, or combinations of these metals. In one or more embodiments, the metal oxide may be zinc or gallium.

The metal oxide may be dispersed on the surfaces of the zeolite support. The surfaces of the zeolite support may include the outer surfaces of the zeolite support as well as the surfaces of the pores extending into the zeolite support. The catalyst composition may include an amount of the metal oxide dispersed on the on the surfaces of the zeolite support that is sufficient to cause at least a portion of the hydrocarbons to undergo chemical reactions to form aromatic hydrocarbons. The catalyst composition may include from 1 wt. % to 50 wt. % metal oxide, based on the total weight of the catalyst composition. For example, the catalyst composition may include from 1 wt. % to 45 wt. %, from 1 wt. % to 40 wt. %, from 1 wt. % to 35 wt. %, from 1 wt. % to 30 wt. %, from 1 wt. % to 25 wt. %, from 5 wt. % to 50 wt. %, from 10 wt. % to 50 wt. %, from 15 wt. % to 50 wt. %, from 20 wt. % to 50 wt. %, from 25 wt. % to 50 wt. %, from 5 wt. % to 25 wt. %, or from 10 wt. % to 20 wt. % metal oxide, based on the total weight of the catalyst composition.

The zeolite support may include faujasite (FAU) zeolites, mordenite framework inverted (MFI) zeolites, Beta (*BEA) zeolites, or combinations of these zeolite types. Framework types are described in, for example, "Atlas of Zeolite Framework Types" by Ch. Baerlocher et al, Fifth Revised Edition, 2001, the teachings of which are incorporated by reference herein.

In embodiments, the zeolites may comprise microstructures (which include micropores) characterized by MFI framework type zeolite. It should be understood that MFI refers to zeolite framework types as identified by its three letter code established by the International Union of Pure and Applied Chemistry (IUPAC). Other framework types are contemplated in the presently disclosed embodiments.

In embodiments, the zeolite support may be a ZSM-5 zeolite. "ZSM-5" generally refers to zeolites having an MFI framework type according to the IUPAC zeolite nomenclature and consisting majorly of silica and alumina, as is understood by those skilled in the art. ZSM-5 refers to "Zeolite Socony Mobil-5" and is a pentasil family zeolite that can be represented by the chemical formula $Na_nAl_nSi_{96-n}O_{196} \cdot 16H_2O$, where $0 < n < 27$.

The aromatization of hydrocarbons is a multi-step reaction involving cracking, oligomerization, isomerization, and cyclization at Brønsted acid sites and the dehydrogenation and/or hydrogen transfer at the Lewis acid sites. Accordingly, in embodiments, the zeolite may be in protonic form. A zeolite in protonic form provides Brønsted acid sites and some Lewis acid sites required for aromatization reaction. The acidity of the zeolite catalyst can be quantitatively determined by the ammonia temperature-programmed desorption ($NH_3$-TPD) method described in ASTM D4824-13.

Along with micropores, which may generally be defined by a framework type of the zeolite, the zeolites may also comprise mesopores. As used herein a "mesoporous zeolite" refers to a zeolite which includes mesopores, and may have an average pore size of from 2 to 50 nm. The presently disclosed mesoporous zeolites may have an average pore size of greater than 2 nm, such as from 4 nm to 16 nm, from 6 nm to 14 nm, from 8 nm to 12 nm, or from 9 nm to 11 nm. In some embodiments, the majority of the mesopores may be greater than 8 nm, greater than 9 nm, or even greater than 10 nm. The mesopores of the mesoporous zeolites described may range from 2 nm to 40 nm, and the median pore size may be from 8 to 12 nm. In embodiments, the mesopore structure of the zeolites may be fibrous, where the mesopores are channel-like. The mesoporous zeolites described may be generally silica-containing materials, such as aluminosilicates, pure silicates, or titanosilicates.

Both dealumination and desilication are post-synthesis modification techniques that can be used to creating mesopores in microporous zeolites. Accordingly, mesoporosity of the zeolite may be enhanced by an acid-leaching treatment, a base-leaching treatment, or a combination of an acid-leaching treatment and a base-leaching treatment. In embodiments, the base-leaching treatment may desilicate the zeolite. Desilication of the zeolite may improve the mesoporosity of the zeolite catalyst by removing weakly bonded $SiO_x$ from the zeolite framework, thereby leading to a lower silica-to-alumina ratio of the zeolite. In embodiments, the acid-leaching treatment may dealuminate the zeolite. Dealumination of the zeolite may improve the mesoporosity of the zeolite by removing weakly bonded $AlO_x$ from the zeolite framework, thereby leading to a higher silica-to-alumina ratio of the zeolite.

Although both desilication and dealumination may have a similar impact on the physical structural properties of the zeolite (e.g., BET surface area and porosity), they may have very different impacts on the chemical properties of the zeolite (e.g., the acidity of the zeolite). Without being bound by theory, it is believed that a change in silica-to-alumina ratio is directly related to a change of zeolite acid site density, where a higher silica-to-alumina ratio corresponds to a lower acid site density. Further, it is believed that site density is a key parameter of the zeolitic aromatization catalyst and as such, a higher acid site density (and a lower silica-to-alumina ratio) leads to higher aromatization activity. In embodiments, the porosity of the zeolite may be enhanced by desilication through base-leaching, as the base-leaching does not harm the Brønsted acid site density of the zeolite catalyst.

Accordingly, in embodiments, the molar ratio of silica to alumina in the ZSM-5 may be at least 5:1. For example, the molar ratio of silica to alumina in the ZSM-5 zeolite may be at least 10:1, at least 12:1, or even at least 30:1, such as from 5:1 to 40:1, from 12:1 to 40:1, or from 5:1 to 80:1. In embodiments, the molar ratio of silica to alumina of the zeolite support may range from 10:1 to 50:1, from 15:1 to 50:1, from 20:1 to 50:1, from 25:1 to 50:1, from 30:1 to 50:1, from 5:1 to 45:1, from 10:1 to 45:1, from 15:1 to 45:1, from 20:1 to 45:1, from 25:1 to 45:1, from 30:1 to 45:1, from 5:1 to 40:1, from 10:1 to 40:1, from 15:1 to 40:1, from 20:1 to 40:1, from 25:1 to 40:1, or from 30:1 to 40:1.

As described above, the catalyst composition may include the metal oxide dispersed across the outer surfaces and pore surfaces of the zeolite support. In one or more embodiments, the catalyst composition may consist of or consist essentially of the metal oxide dispersed onto the outer surfaces and pore surfaces of the zeolite support. The catalyst composition may have a BET surface area of from 100 square meters per gram ($m^2/g$) to 600 $m^2/g$, such as from 150 $m^2/g$ to 550 $m^2/g$, from 200 $m^2/g$ to 500, from 250 $m^2/g$ to 450 $m^2/g$, from 300 $m^2/g$ to 400 $m^2/g$, from 305 $m^2/g$ to 390 $m^2/g$, from 310 $m^2/g$ to 380 $m^2/g$, from 310 $m^2/g$ to 370 $m^2/g$, from 310 $m^2/g$ to 360 $m^2/g$, from 310 $m^2/g$ to 350 $m^2/g$, from 310 $m^2/g$ to 340 $m^2/g$, from 310 $m^2/g$ to 330 $m^2/g$, or from 310 $m^2/g$ to 320 $m^2/g$. The catalyst composition may have an average pore diameter of from 5.0 nanometers (nm) to 50.0 nm, such as from 5.0 nm to 40.0 nm, from 5.0 nm to 30.0 nm, from 5.0 nm to 20.0 nm, from 5.0 nm to 10.0 nm, from 5.0 nm to 9.0 nm, from 5.0 nm to 8.0 nm, from 5.0 nm to 7.5 nm, from 5.0 nm to 7.0 nm, from 6.0 nm to 40.0 nm, from 6.0 nm to 30.0 nm, from 6.0 nm to 20.0 nm, from 6.0 nm to 10.0 nm, from 6.0 nm to 9.0 nm, from 6.0 nm to 8.0 nm, from 6.0 nm to 7.5 nm, or from 6.0 nm to 7.0 nm.

Without being bound by theory, it is believed that the accessibility of reactant molecules to catalyst active sites can be improved by enhancing mesoporosity of the aromatization catalyst. With improved accessibility of reactant molecules to catalyst active sites, thermal cracking during direct aromatization is minimized, therefore formation of coking precursors is effectively suppressed, and aromatization catalyst activity and stability are subsequently improved. Accordingly, the catalyst composition may have a mesopore volume of greater than 0.090 $cm^3/g$. In embodiments, the catalyst composition may have a mesopore volume of greater than or equal to 0.090 $cm^3/g$, greater than or equal to 0.091 $cm^3/g$, greater than or equal to 0.092 $cm^3/g$, greater than or equal to 0.093 $cm^3/g$, greater than or equal to 0.094 $cm^3/g$, greater than or equal to 0.095 $cm^3/g$, greater than or equal to 0.096 $cm^3/g$, greater than or equal to 0.097 $cm^3/g$, greater than or equal to 0.098 $cm^3/g$, greater than or equal to 0.099 $cm^3/g$, greater than or equal to 0.100 $cm^3/g$, or even greater than or equal to 0.101 $cm^3/g$, and less than or equal to 0.200 $cm^3/g$.

Surface area, pore volume, average pore size, and pore size distribution may be measured by $N_2$ adsorption isotherms performed at 77 Kelvin (K) (such as with a Micrometrics ASAP 2020 system). As would be understood by those skilled in the art Brunauer, Emmett, and Teller (BET) analysis methods may be utilized to calculate the surface area, and the Barrett, Joyner and Halenda (BJH) calculation may be used to determine pore volume and pore size distribution.

In embodiments, the crystalline particles of the zeolite support have an average "crystal size" measured by powder X-ray diffraction (XRD) method. The zeolite crystalline particles may have a crystal size from 25 nm to 500 nm, from 50 nm to 400 nm, from 100 nm to 300 nm, or less than 900 nm, less than 800 nm, less than 700 nm, less than 600 nm, less than 500 nm, less than 400 nm, less than 300 nm, or less than 250 nm.

The catalyst composition may be formed as an assembly of zeolite crystallites. The crystalline structure of the catalyst composition may have a branched, fibrous structure with highly interconnected intra-crystalline mesopores. Such structures may be advantageous in applications where the structural integrity of the catalyst composition is important while the ordering of the mesopores is not.

According to one or more embodiments, the catalysts described in the present disclosure may be produced by treating a protonic form of a zeolite with a base-leaching process to enhance its porosity. Protonic forms of zeolites can be prepared according to any method known and used in the art, such as by calcining a commercially-available ammonium form zeolite powder sample. In a typical base-leaching process, the protonic zeolite is placed in a flask with an alkaline solution (e.g., NaOH) to form a slurry suspension, which is then heated while being stirred.

Following base-leaching, the zeolite may be converted back to the protonic form through ion-exchanges, such as is described in Verboekend, D., Mitchell, S., Milina, M., Groen, J. C., Perez-Ramirez, J. "Full compositional flexibility in the preparation of mesoporous MFI zeolites by desilication," J. Phys. Chem C. 115, 14193-14203 (2011), the entire contents of which is hereby incorporated by reference in its entirety.

The zeolite support having an enhanced mesoporosity may then be doped with a metal modifier (e.g., zinc or gallium) to disperse the metal modifier on the zeolite support, thereby forming the catalyst. In embodiments, the metal modifier is dispersed on the zeolite support by mixing the zeolite support with a solution containing the metal element. For example, an appropriate amount of aqueous solution of zinc nitrate or gallium nitrate with an appropriate concentration may be mixed with the zeolite support. The zeolite support impregnated with the precursor, i.e. zinc nitrate or gallium nitrate, of metal modifier, i.e. zinc or gallium, is dried, calcined, and shaped to form the catalyst. It is contemplated that any one of a variety of processes can be used to disperse the metal modifiers on the zeolite support, including, but not limited to, impregnation, ion-exchange, precipitation, chemical fusion, or chemical vapor deposition.

Aromatization catalyst compositions that are formed for aromatization of light naphthas described herein comprise an effective amount of one or more inorganic oxide components, an effective amount of one or more zeolite components as described herein, and in certain embodiments an effective amount of one or more active components.

The inorganic oxide component excludes the herein zeolite, and typically contains a substance serving as a granulating agent or a binder. Usually, a known substance can be used as a granulating agent or binder for the aromatization catalyst herein. As the inorganic oxide, a porous inorganic oxide used in aromatization catalyst compositions in the related art can be used. Examples thereof include alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia. In certain embodiments of the process for aromatization of light naphtha as described herein, an inorganic oxide component comprising alumina, silica-alumina or a combination of alumina and silica-alumina is used in the aromatization catalyst compositions.

The catalyst extrudate may be in the form of cylinder, trilobe, quadralobe, or spheres for fixed-bed reactor configurations or spray dried particles for fluidized-bed configuration.

In embodiments, the zeolite content of the catalyst composition may be in the range 1-80 wt. % based on a total weight of the catalyst composition.

The catalyst composition of the present disclosure may be utilized in a process to convert hydrocarbons to one or more aromatic compounds. The process of the present disclosure for aromatizing hydrocarbons may include contacting hydrocarbons with a catalyst composition comprising a metal oxide dispersed on a surface of a zeolite support within a catalyst system, where contacting the hydrocarbons with the catalyst composition causes at least a portion of the hydrocarbons to undergo chemical reactions to form aromatic hydrocarbons. The process for converting hydrocarbons to aromatic compounds may further include pretreating the catalyst composition formed according to any of the previously described embodiments. Pretreating the catalyst composition may improve catalyst composition's ability to aromatize hydrocarbons. The catalyst composition may be pretreated under nitrogen and/or hydrogen flow at a temperature from 400° C. to 700° C. For example, the pretreatment temperature may be from 425° C. to 700° C., from 450° C. to 700° C., from 475° C. to 700° C., from 500° C. to 700° C., from 525° C. to 700° C., from 550° C. to 700° C., from 400° C. to 675° C., from 400° C. to 650° C., from 400° C. to 625° C., from 400° C. to 600° C., from 425° C. to 675° C., from 450° C. to 650° C., from 475° C. to 625° C., from 500° C. to 600° C., or from 525° C. to 575° C. The pretreatment of the catalyst composition may be conducted for a duration from 1.0 hour to 5.0 hours, such as from 1.5 hours to 5.0 hours, from 2.0 hours to 5.0 hours, from 2.5 hours to 5.0 hours, from 1.0 hour to 4.5 hours, from 1.0 hour to 4.0 hours, from 1.0 hour to 3.5 hours, from 1.5 hours to 4.5 hours, from 2.0 hours to 4.0 hours, or from 2.5 hours to 3.5 hours.

Following pretreatment of the catalyst composition, the hydrocarbon feed may be contacted with the catalyst composition under reaction conditions sufficient to cause at least a portion of the hydrocarbons to undergo chemical reactions to form aromatic hydrocarbons. The contacting may occur within a catalyst system and will now be described.

Referring now to FIGS. 1A and 1B, an embodiment of the catalyst system for producing aromatic hydrocarbons from a hydrocarbon feed containing non-aromatic hydrocarbons is illustrated, the catalyst system being designated by reference number 100. In FIG. 1A, the catalyst system 100 is configured as an upflow reactor, while in FIG. 1B, the catalyst system 100 is configured as a downflow reactor. The catalyst system 100 may include a reaction zone 110. In one or more embodiments, the reaction zone 110 may be a portion of a reactor that includes the catalyst composition 112 prepared by the synthesis process of the present disclosure. The catalyst system 100 may include one or a plurality of reactors. The reactor or reactors of the catalyst system 100 may include but are not limited to tank or tubular reactors, which may be configured to operate as a batch reactor, a fixed-bed reactor, a continuous stirred-tank reactor (CSTR), or a plug flow reactor. As depicted in FIGS. 1A and 1B, the hydrocarbon feed 102 including one or more non-aromatic hydrocarbons may be introduced to the reaction zone 110, and reactor effluent 114 may be passed out of the reaction zone 110 following contact of the hydrocarbons of the hydrocarbon feed 102 with the catalyst composition 112 in the reaction zone 110. Contacting the hydrocarbons present in the hydrocarbon feed 102 with the catalyst composition 112 in the reaction zone 110 may cause at least a portion of the hydrocarbons from the hydrocarbon feed 102 to undergo a chemical reaction to form aromatic hydrocarbons, which may be present in the reactor effluent 114. The reactor effluent 114 comprising the aromatic hydrocarbons may be passed out of the reaction zone 110.

The hydrocarbon feed 102 may be contacted with the catalyst composition 112 in the reaction zone 110 under reaction conditions sufficient to cause at least a portion of the hydrocarbons to undergo a chemical reaction to form aromatic hydrocarbons. The hydrocarbon feed 102 may be contacted with the catalyst composition 112 in the reaction zone 110 at a reaction temperature from 200° C. to 900° C., such as from 250° C. to 850° C., from 300° C. to 800° C., from 350° C. to 750° C., from 400° C. to 700° C., from 450° C. to 650° C., from 475° C. to 625° C., from 500° C. to 600° C., from 525° C. to 575° C., or at 550° C. The hydrocarbon feed 102 may be contacted with the catalyst composition 112 in the reaction zone 110 at a pressure from 1 bar to 30 bars, such as from 1 bar to 25 bars, from 1 bar to 20 bars, from 1 bar to 15 bars, from 1 bar to 10 bars, or at 5 bars. The hydrocarbon feed 102 may be contacted with the catalyst composition 112 in the reaction zone 110 at a weight hourly space velocity (WHSV) from 0.1 per hour to 20.0 per hour, such as from 0.25 per hour to 15.0 per hour, from 0.5 per hour to 10.0 per hour, from 0.75 per hour to 5.0 per hour, from 0.75 per hour to 2.0 per hour, or from 0.75 per hour to 1.25 per hour.

The reactor effluent 114 may include one or a plurality of aromatic hydrocarbons, such as but not limited to benzene, toluene, ethylbenzene, mixed xylenes (ortho-xylene, meta-xylene, para-xylene, or mixtures of these), and combinations of such hydrocarbons. Benzene, toluene, ethylbenzene, and mixed xylenes may be collectively referred to as "BTEX." In one or more than one embodiment, at least 70% of the hydrocarbons from the hydrocarbon feed undergo chemical reactions to form aromatic hydrocarbons, such as at least 70.5%, at least 71%, at least 71.5%, at least 72%, at least 72.5%, at least 73%, at least 73.5%, at least 74%, at least 74.5%, or at least 75%. In one or more embodiments, at least 60% of the hydrocarbons undergo a chemical reaction to form BTEX hydrocarbons, such as at least 60.25%, at least 60.5%, at least 60.75%, at least 61%, at least 61.25%, at least 61.5%, at least 61.75%, at least 62%, at least 62.25%, at least 62.5%, at least 62.75%, or at least 63%.

EXAMPLES

The following examples illustrate one or more additional features of the present disclosure described previously. It should be understood that these examples are not intended to limit the scope of the disclosure or the appended claims in any manner.

In the following examples, aromatization catalyst compositions were prepared according to a variety of techniques and characterized for the suitability for aromatizing hydrocarbons.

Example 1

An as-received commercial ammonium form MFI zeolite powder sample, CBV3024E by Zeolyst, was calcined at 500° C. for 5 hours to form hydrogen form zeolite, coded as Z30. The calcined Z30 zeolite sample was treated by a base-leaching process to enhance its mesoporosity. In a typical base-leaching experiment, 5 grams of calcined Z30 zeolite powder was placed in a round bottom flask, to which 50 mL alkaline solution (0.2 M NaOH) was added to form a slurry suspension. The slurry suspension was heated to 80° C. while being stirred with a magnetic stirrer, and kept at 80° C. for 60 min. Following the base-leaching treatment, the slurry suspension was cooled down, and the zeolite solid was filtered out and washed thoroughly with deionized water until pH neutral. The zeolite solid was then transferred to a drying oven and kept at 110° C. overnight.

The base-leached zeolite was converted back to the protonic form by three consecutive ion exchanges with 1.0 M aqueous $NH_4NO_3$ solution at 80° C. according to a procedure described in Verboekend, D. et al. The ammonium-exchanged zeolite was dried at 110° C. overnight, and calcined at 550° C. for 5 hours. The resulting base-leached zeolite sample in protonic form was coded as DS1. Table 1 compares textual properties of the zeolite samples before and after the base-leaching treatment.

TABLE 1

Textual properties of zeolite samples before and after base-leaching treatment.

| Catalyst Sample | BET area $[m^2/g]$ | Micro-pore volume $[cm^3/g]$ | Meso-pore volume $[cm^3/g]$ | Average pore diameter [nm] | $SiO_2/Al_2O_3$ ratio |
|---|---|---|---|---|---|
| Z30 | 342 | 0.170 | 0.058 | 5.05 | 37.2 |
| DS1 | 343 | 0.217 | 0.106 | 6.32 | 36.9 |
| Zn/DS1 | 318 | 0.209 | 0.104 | 6.82 | — |
| Ga/DS1 | 307 | 0.202 | 0.102 | 6.74 | — |

As shown in Table 1, desilication increased the BET surface area, the micropore volume, the mesopore volume, and the average pore diameter of the catalyst.

The zeolite powder samples were pelletized and sieved to a particle size of from 500 μm to 1000 μm for use in the remaining examples.

Example 2

Gallium nitrate (0.3668 g) was dissolved in 5 mL deionized water to form an aqueous gallium nitrate solution in a beaker, to which 5 grams of desilicated zeolite powder, DS1, was added. The mixture was stirred with a magnetic stirrer for 1 hour to obtain a homogenous slurry mixture. Water was subsequently removed from the mixture by keeping the mixture on a hot plate at a temperature of about 50° C. under stirring. The dry paste was transferred to an oven at a temperature of 110° C. for 12 hours, and was further calcined at 550° C. for 6 hours. The catalyst sample was pelletized and sieved to a particle size of from 500 μm to 1000 μm and labeled as Ga/DS1. The BET area, micropore volume, mesopore volume, and average pore diameter of the sample are reported in Table 1.

Example 3

Zinc nitrate hydrate (0.2275 g) was dissolved in 5 mL deionized water to form an aqueous zinc nitrate hydrate solution in a beaker, to which 5 grams of desilicated zeolite powder, DS1, was added. The mixture was stirred with a magnetic stirrer for 1 hour to obtain a homogenous slurry mixture. Water was subsequently removed from the mixture by keeping the mixture on a hot plate at a temperature of about 50° C. under stirring. The dry paste was transferred to an oven at a temperature of 110° C. for 12 hours, and was further calcined at 550° C. for 6 hours. The catalyst sample was pelletized and sieved to a particle size of from 500 μm to 1000 μm and labeled as Zn/DS1. The BET area, micropore volume, mesopore volume, and average pore diameter of the sample are reported in Table 1.

Example 4

Catalyst samples were tested in a laboratory scale fixed-bed reactor using a hydrotreated light naphtha feed. The hydrotreated light naphtha feed contained 43 ppm sulfur, and had a density of 0.6764 $g/cm^3$. Table 2 shows results of a detailed hydrocarbon analysis of the feed sample.

TABLE 2

Detailed hydrocarbon analysis of the feed sample.

| Carbon # | n-Paraffins | iso-Paraffins | Olefins | Naphthenes | Aromatics | Total |
|---|---|---|---|---|---|---|
| C5 | 13.9 | 14.9 | 0.0 | 3.6 | 0.0 | 32.4 |
| C6 | 14.9 | 27.8 | 0.0 | 4.4 | 3.3 | 50.5 |
| C7 | 0.0 | 16.8 | 0.2 | 0.1 | 0.0 | 17.1 |
| Total | 28.8 | 59.6 | 0.2 | 8.1 | 3.3 | 100.0 |

Additional comparative catalyst samples were prepared by doping the Z30 catalyst with zinc or gallium by a conventional wet impregnation process. To prepare a 1% zinc-doped catalyst, 0.4549 g of precursor zinc nitrate was dissolved in 100 mL deionized water. The zinc nitrate solution was added to 10 g of Z30 powder. The mixture was put under continuous stirring at 250 rpm and room temperature for 3 hours. Excess water was further removed by slow evaporation of the resulting mixture at 60° C. under stirring. The product was dried overnight at 100° C. followed by calcination in a muffle furnace at 550° C. for 6 hours, pelletized, and sieved to particle size of from 500 μm to 1000 μm, and labeled as Zn/Imp.

To prepare a 2% gallium-doped catalyst, 0.7336 g of precursor gallium nitrate was dissolved in 100 mL deionized water. The gallium nitrate solution was added to 10 g of Z30 powder. The mixture was put under continuous stirring at 250 rpm and room temperature for 3 hours. Excess water was further removed by slow evaporation of the resulting mixture at 60° C. under stirring. The product was dried overnight at 100° C. followed by calcination in a muffle furnace at 550° C. for 5 hours, pelletized, and sieved to particle size of from 500 μm to 1000 μm, and labeled as Ga/Imp.

For each of the Z30, DS1, Ga/Imp, Zn/Imp, Ga/DS1, and Zn/DS1 catalysts, 0.5 grams of catalyst granules with a size range of from 0.5 mm to 1.0 mm were loaded in a stainless steel tube reactor (grade 316, ø8×14 mm). The catalyst was heated to 550° C. in a nitrogen flow. While keeping a constant $N_2$ flow of 10 mL/min, the light naphtha feed was introduced to the reactor through a liquid syringe pump to start the reaction. The reaction was kept running at 550° C., atmospheric pressure, and weight hourly space velocity (WHSV) of 1-4.2 $h^{-1}$. The reaction products were analyzed using an on-line GC equipped with two FIDs.

TABLE 3

Comparison of aromatization product yields using mesoporous catalysts.

| Product Yield | Z30 | DS1 | Ga/DS1 | Ga/Imp | Zn/DS1 | Zn/Imp |
|---|---|---|---|---|---|---|
| Meso-pore volume (cm³/g) | 0.058 | 0.106 | 0.104 | 0.102 | 0.104 | 0.092 |
| Benzene | 25.8 | 17.9 | 32.3 | 13.8 | 32.7 | 25.2 |
| Toluene | 23.7 | 34.5 | 34.1 | 27.7 | 26.9 | 28.4 |
| Ethylbenzene | 0.6 | 1.0 | 0.0 | 0.00 | 0.3 | 0.0 |
| Xylenes | 7.5 | 15.0 | 11.1 | 17.7 | 9.5 | 4.1 |
| C9+ aromatics | 0.5 | 0.6 | 2.3 | 11.6 | 1.4 | 0.0 |
| Methane | 4.6 | 6.4 | 6.1 | 7.2 | 3.6 | 8.6 |
| C2 (ethane + ethylene) | 4.5 | 5.8 | 4.8 | 9.6 | 5.4 | 11.5 |
| C3 + C4 | 32.6 | 18.6 | 9.3 | 12.3 | 20.2 | 22.2 |
| Total aromatics | 58.2 | 69.1 | 79.8 | 70.8 | 70.8 | 58.2 |

The DS1 zeolite catalyst with enhanced mesoporosity (Zn/DS1) showed an improved total aromatics yield (69.1 wt. %) compared to Z30 (58.2 wt. %). Among the tests with different metal-modified zeolite catalysts with enhanced mesoporosity, both Zn/DS1 and Ga/DS1 showed a very remarkable aromatization activity. Specifically, Zn/DS1 showed a total aromatics yield of 70.8 wt. % and a BTX yield of 69.4 wt. %, while Ga/DS1 showed a total aromatics yield of 79.8 wt. % and a BTX yield of 77.5 wt. %. In contrast, the 2% Ga/Imp reference catalyst showed a total aromatics yield of 70.8 wt. % and a BTX yield of 59.2 wt. %, and the 1% Zn/Imp reference catalyst showed a total aromatics yield of 58.2 wt. % and a BTX yield of 57.7 wt. %.

According to a first aspect of the present disclosure, a process for aromatizing hydrocarbons comprises contacting the hydrocarbons with a catalyst comprising a zinc- or gallium-doped ZSM-5 catalyst having a mesopore volume of greater than 0.09 $cm^3/g$, wherein contacting the hydrocarbons with the catalyst causes a least a portion of the hydrocarbons to undergo chemical reactions to form aromatic hydrocarbons.

According to a second aspect of the present disclosure, a process for aromatizing hydrocarbons comprises the process according to the first aspect, wherein a mesoporosity of the zeolite is enhanced by a base-leaching treatment, an acid leaching treatment, or both.

According to a third aspect of the present disclosure, a process for aromatizing hydrocarbons comprises the process according to any one of the preceding aspects, wherein the hydrocarbons have 2 carbon atoms to 12 carbon atoms.

According to a fourth aspect of the present disclosure, a process for aromatizing hydrocarbons comprises the process according to any one of the preceding aspects, wherein the hydrocarbons comprise paraffins, olefins, naphthenes, alkylbenzenes, and combinations thereof.

According to a fifth aspect of the present disclosure, a process for aromatizing hydrocarbons comprises the process according to any one of the preceding aspects, wherein the hydrocarbons comprise paraffinic hydrocarbons have from 4 carbon atoms to 7 carbon atoms.

According to a sixth aspect of the present disclosure, a process for aromatizing hydrocarbons comprises the process according to any one of the preceding aspects, wherein the zinc- or gallium-doped ZSM-5 catalyst comprises from 1 wt. % to 30 wt. % metal dopant.

According to a seventh aspect of the present disclosure, a process for aromatizing hydrocarbons comprises the process according to any one of the preceding aspects, wherein the zinc- or gallium-doped ZSM-5 catalyst comprises from 2 wt. % to 5 wt. % metal dopant.

According to an eighth aspect of the present disclosure, a process for aromatizing hydrocarbons comprises the process according to any one of the preceding aspects, further comprising: pre-treating the zinc- or gallium-doped ZSM-5 catalyst under a flow of hydrogen or nitrogen at a temperature from 400° C. to 700° C. for a duration from 1 to 5 hours.

According to a ninth aspect of the present disclosure, a process for aromatizing hydrocarbons comprises the process according to any one of the preceding aspects, wherein the hydrocarbons comprise straight run light naphtha.

According to a tenth aspect of the present disclosure, a process for aromatizing hydrocarbons comprises the process according to any one of the preceding aspects, wherein the hydrocarbons comprise aromatic and naphthenic hydrocarbons in minor proportions by volume.

According to an eleventh aspect of the present disclosure, a process for aromatizing hydrocarbons comprises the process according to any one of the preceding aspects, wherein the contacting the hydrocarbons with the catalyst is performed at a weight hourly space velocity (WHSV) from 1.0 to 20.0 h$^{-1}$, a temperature from 200° C. to 600° C., and a pressure from 1.0 bar to 30.0 bars.

According to a twelfth aspect of the present disclosure, a process for aromatizing hydrocarbons comprises the process according to any one of the preceding aspects, wherein the catalyst is formed from a desilicated ZSM catalyst.

According to a thirteenth aspect of the present disclosure, a process for aromatizing hydrocarbons comprises the process according to any one of the preceding aspects, wherein the aromatic hydrocarbons comprise benzene, toluene, ethylbenzene, xylene, or combinations thereof.

According to a fourteenth aspect of the present disclosure, a process for aromatizing hydrocarbons comprises the process according to any one of the preceding aspects, wherein the catalyst has a silica to alumina molar ratio from 5:1 to 50:1.

According to a fifteenth aspect, a process of forming a catalyst for aromatizing hydrocarbons comprises: enhancing a mesoporosity of a zeolite support by a base-leaching treatment, an acid-leaching treatment, or both to form a zeolite support having enhanced mesoporosity; mixing the zeolite support having enhanced mesoporosity with a solution containing zinc or gallium to disperse the zinc or gallium on the zeolite support having enhanced mesoporosity; and calcining the zeolite support having enhanced mesoporosity with zinc or gallium dispersed thereon to form a zinc- or gallium-doped zeolite catalyst having a mesopore volume of greater than 0.09 cm$^3$/g.

According to a sixteenth aspect of the present disclosure, a process of forming a catalyst for aromatizing hydrocarbons comprises the process according to the fifteenth aspect, wherein the zeolite support comprises a ZSM-5 support.

According to an seventeenth aspect of the present disclosure, a process of forming a catalyst for aromatizing hydrocarbons comprises the process according to the fifteenth or sixteenth aspect, wherein enhancing the mesoporosity of the zeolite support comprises treating the zeolite support with a base-leaching process.

According to a eighteenth aspect of the present disclosure, a process of forming a catalyst for aromatizing hydrocarbons comprises the process according to any one of the fifteenth through seventeenth aspects, wherein zinc- or gallium-doped zeolite catalyst comprises from 1 wt % to 30 wt % metal dopant.

According to a nineteenth aspect of the present disclosure, a process of forming a catalyst for aromatizing hydrocarbons comprises the process according to any one of the fifteenth through eighteenth aspects, wherein the zinc- or gallium-doped zeolite catalyst has a silica to alumina molar ratio from 5:1 to 50:1.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

According to a twentieth aspect of the present disclosure, a process of forming a catalyst for aromatizing hydrocarbons comprises the process according to any one of the fifteenth through nineteenth aspects, wherein the process yields greater than or equal to 80% by weight of aromatic hydrocarbons.

What is claimed is:

1. A process for aromatizing hydrocarbons comprising:
   contacting the hydrocarbons with a catalyst comprising a zinc- or gallium-doped ZSM-5 zeolite having a mesopore volume of greater than 0.09 cm$^3$/g and less than 0.20 cm$^3$/g, wherein the ZSM-5 zeolite is desilicated, wherein contacting the hydrocarbons with the catalyst causes a least a portion of the hydrocarbons to undergo chemical reactions to form aromatic hydrocarbon products, and wherein at least 60% of the hydrocarbons form benzene, toluene, ethylbenzene, xylene, or combinations thereof.

2. The process according to claim 1, wherein the hydrocarbons have 2 carbon atoms to 12 carbon atoms.

3. The process according to claim 2, wherein the hydrocarbons comprise paraffins, olefins, naphthenes, alkylbenzenes, and combinations thereof.

4. The process according to claim 3, wherein the hydrocarbons comprise paraffinic hydrocarbons have from 4 carbon atoms to 7 carbon atoms.

5. The process according to claim 1, wherein the catalyst comprises from 1 wt. % to 30 wt. % zinc and/or gallium dopant.

6. The process according to claim 1, wherein the catalyst comprises from 2 wt. % to 5 wt. % zinc and/or gallium dopant.

7. The process according to claim 1, further comprising:
   treating the desilicated zinc- or gallium-doped ZSM-5 zeolite under a flow of hydrogen or nitrogen at a temperature from 400° C. to 700° C. for a duration from 1 to 5 hours before contacting the hydrocarbons with the catalyst.

8. The process according to claim 1, wherein the hydrocarbons comprise straight run light naphtha.

9. The process according to claim 1, wherein the hydrocarbons comprise aromatic and naphthenic hydrocarbons in minor proportions by volume.

10. The process according to claim 1, wherein the contacting the hydrocarbons with the catalyst is performed at a weight hourly space velocity (WHSV) from 1.0 to 20.0 h$^{-1}$, a temperature from 200° C. to 600° C., and a pressure from 1.0 bar to 30.0 bars.

11. The process according to claim 1, wherein the aromatic hydrocarbon products comprise benzene, toluene, ethylbenzene, xylene, or combinations thereof.

12. The process according to claim 1, wherein the desilicated zinc- or gallium-doped ZSM-5 zeolite has a silica to alumina molar ratio from 5:1 to 50:1.

13. The process according to claim 1, wherein the ZSM-5 zeolite is doped with zinc or gallium after desilication of the ZSM-5 zeolite.

14. The process according to claim 1, wherein the catalyst has a BET surface area of from 100 $m^2/g$ to 380 $m^2/g$.

* * * * *